(12) United States Patent
Suzuki et al.

(10) Patent No.: US 8,605,278 B2
(45) Date of Patent: Dec. 10, 2013

(54) METHOD AND APPARATUS FOR INSPECTING PATTERNED MEDIA DISK

(75) Inventors: Ryuta Suzuki, Kamisato (JP); Yu Yanaka, Kamisato (JP); Yu Kusaka, Kamisato (JP)

(73) Assignee: Hitachi High-Technologies Corporation, Tokyo (JP)

( * ) Notice: Subject to any disclaimer, the term of this patent is extended or adjusted under 35 U.S.C. 154(b) by 26 days.

(21) Appl. No.: 13/332,598

(22) Filed: Dec. 21, 2011

(65) Prior Publication Data

US 2012/0154798 A1 Jun. 21, 2012

(30) Foreign Application Priority Data

Dec. 21, 2010 (JP) ................................ 2010-284739

(51) Int. Cl.
*G01N 21/00* (2006.01)
(52) U.S. Cl.
USPC ...................................................... 356/237.5
(58) Field of Classification Search
USPC ...................................................... 356/237.5
See application file for complete search history.

(56) References Cited

U.S. PATENT DOCUMENTS

| 6,011,618 | A | 1/2000 | Iwata et al. |
| 2004/0072499 | A1* | 4/2004 | Wakabayashi ..................... 451/5 |
| 2009/0067959 | A1* | 3/2009 | Takahashi et al. ........ 414/226.01 |
| 2009/0224151 | A1* | 9/2009 | Hatakeyama et al. ......... 250/307 |

FOREIGN PATENT DOCUMENTS

| JP | 11-183394 A | 7/1999 |
| JP | 2008-32415 A | 2/2008 |

\* cited by examiner

*Primary Examiner* — Tu Nguyen
(74) *Attorney, Agent, or Firm* — Mattingly & Malur, PC

(57) ABSTRACT

In an inspection apparatus that inspects both surfaces of a patterned media disk, to perform inspection while maintaining a high level of throughput, a patterned media disk inspection apparatus of the present invention includes an optical inspection unit, a table unit that includes plural substrate rotation drive units on which a substrate is mounted and rotated and rotates and conveys the substrates mounted on the substrate rotation drive units between a position at which the substrate is inspected by the optical inspection unit and a position at which the substrate is taken out and supplied, a substrate reversing unit, a cassette unit that accommodates substrates, and a substrate handling unit that takes out an uninspected substrate from the cassette unit and supplies the uninspected substrate to the table unit, and further stores a substrate, both surfaces of which have already been inspected, in the cassette unit.

3 Claims, 10 Drawing Sheets

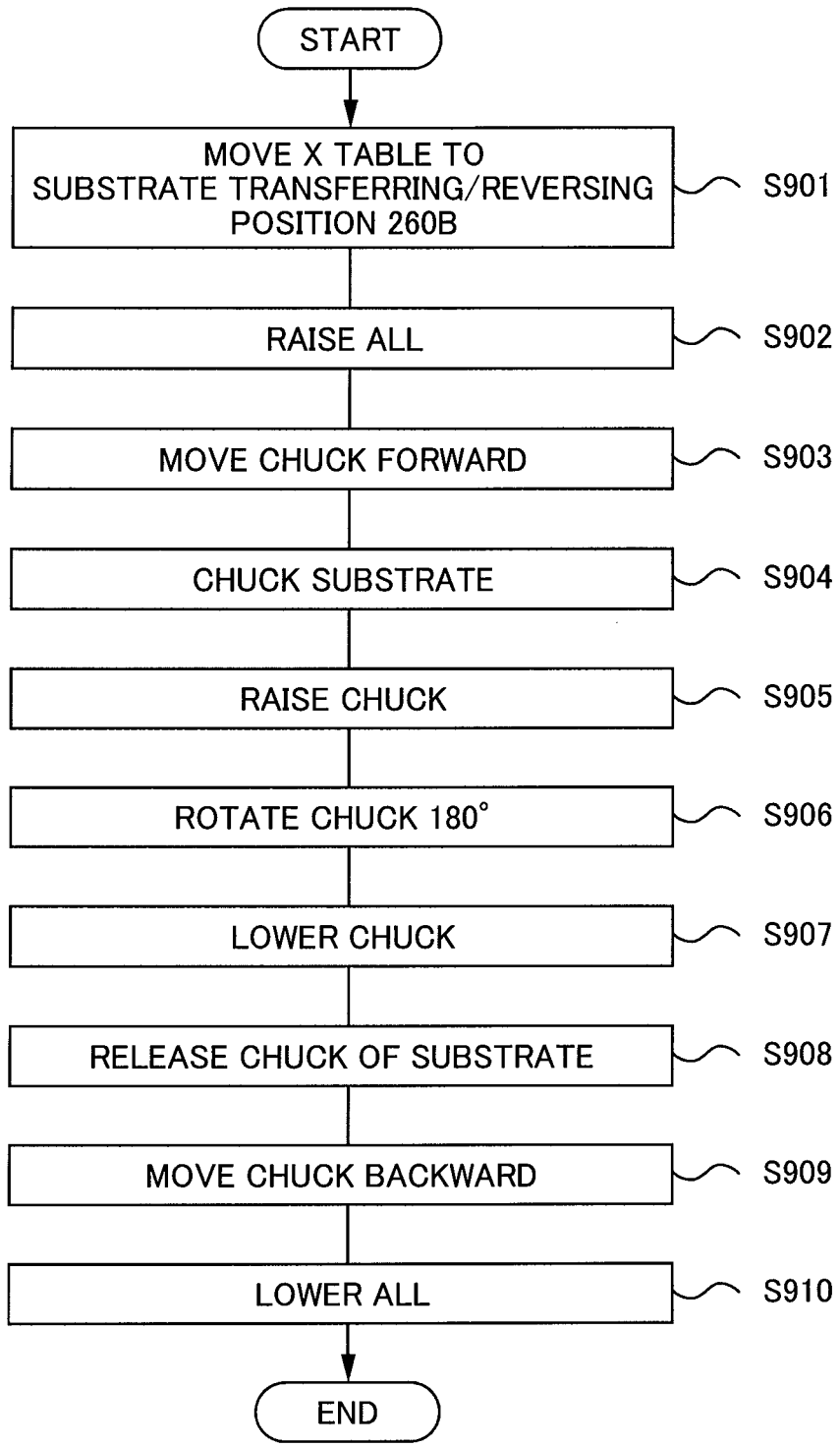

METHOD AND APPARATUS FOR INSPECTING PATTERNED MEDIA DISK

BACKGROUND

The present invention relates to an inspection apparatus for inspecting surfaces of a patterned media disk, in particular to an inspection apparatus and an inspection method suitable for optically inspecting scratches and foreign objects on both sides of a patterned media disk.

In recent years, an amount of information stored on a hard disk, which is used as a recording medium of a personal computer (PC), server, mobile device, and the like, significantly increases, and to cope with this, a perpendicular magnetic recording method is developed as a high density recording method. Currently, it is required to further improve recording density of hard disks. However, in the perpendicular magnetic recording method, as the recording density increases, the influence of magnetic interference between adjacent tracks becomes considerable. As a next-generation recording method to solve the above problem, a patterned media, which is a recording medium made by forming a pattern on a surface of a disk, is studied.

To form patterned media, nanoimprint technology is studied in which a nano-meter level pattern can be mass produced at low cost. In the nanoimprint technology, a pattern formed on a material is pressed onto a disk, on both sides of which a magnetic film layer is formed and a resist is coated thereon, the pattern shape on the material is transferred to the resist, the resist is exposed and developed, and an etching process is performed, so that a pattern of magnetic film layer is formed on both sides of the disk.

When inspecting a pattern of a patterned media disk formed in this way, inspection time increases because smaller defects need to be detected as compared with related art. However, the throughput of the inspection needs to be maintained at the same level as that in related art. To cope with this, it is necessary to shorten handling time to take a patterned media disk in and out an inspection apparatus and reverse a substrate.

A magnetic film is formed on both sides of a substrate of a magnetic disk including a patterned media disk, so that both sides of the substrate needs to be inspected at the same level of accuracy. To inspect both sides, a method is performed in which one side of the substrate is inspected first, then the substrate is reversed, and the other side is inspected. As a method for sequentially inspecting two sides of the substrate one by one, Japanese Patent Application Laid-Open Publication No. 2008-32415 (Patent Document 1) describes a configuration in which, in an inspection apparatus including a handling robot and two spindles, the handling robot reverses a disk, which is mounted on a first spindle and one side of which has been inspected, mounts the disk on a second spindle, removes the disk from the second spindle when the other side has been inspected, and conveys the disk to an ejection position.

Japanese Patent Application Laid-Open Publication No. 11-183394 (Patent Document 2) describes a disk surface inspection apparatus in which two inspection devices are included and front surfaces of two disks are inspected at the same time by one inspection device, and thereafter the disks are reversed by a reversing device and back surfaces of two disks are inspected at the same time by the other inspection device.

SUMMARY

To maintain the throughput of the inspection and secure a high level of inspection accuracy, it is important to use a method that processes plural disks in parallel by using plural inspection heads or a method that secures an inspection time as much as possible by reducing handling time to take a disk in and out an inspection apparatus and reverse a disk.

The invention described in Patent Document 1 has only one inspection head, so that, when the inspection time needs to be increased than before to inspect smaller pattern defects, the increased inspection time directly affects the throughput, so it is not considered to improve the total throughput.

In the invention described in Patent Document 2, it is possible to improve the throughput of the entire apparatus by a configuration in which two inspection units that inspect two substrates at the same time are connected in series and a unit for reversing the substrates is arranged between the inspection units. However, the price of the apparatus is expensive because a total of four optical inspection heads are used. Further, if one inspection unit fails, the entire apparatus stops, so that, as a result, the throughput may be degraded.

The present invention provides a patterned media disk inspection apparatus and a patterned media disk inspection method that can perform inspection of both sides of a patterned media disk while maintaining a high level of throughput.

To solve the above-described problems, the present invention provides a patterned media disk inspection apparatus including an optical inspection unit that emits light to one surface of a substrate, on both surfaces of which a pattern of a resist film is formed, detects a spectrum of light reflected from the pattern, and inspects the pattern, a table unit including plural substrate rotation drive units on which the substrate is mounted and rotated, the table unit rotating and conveying the substrates mounted on the substrate rotation drive units between a position at which the substrate is inspected by the optical inspection unit and a position at which the substrate is taken out and supplied, a substrate reversing unit that removes the substrate, which is mounted on the substrate rotation drive unit and one surface of which is inspected by the optical inspection unit and further which is rotated and conveyed to the position at which the substrate is taken out and supplied by the table unit, from the substrate rotation drive unit and reverses the substrate, and thereafter mounts again the substrate on the substrate rotation drive unit, a cassette unit including a cassette that accommodates a substrate that has not yet been inspected and a cassette that accommodates a substrate that has already been inspected, and a substrate handling unit that takes out an uninspected substrate from a cassette that accommodates a substrate that has not yet been inspected and supplies the uninspected substrate to the substrate rotation drive unit of the table unit, and further takes out a substrate, both surfaces of which have already been inspected by the optical inspection unit, from the substrate rotation drive unit and stores the substrate in the cassette that accommodates a substrate that has already been inspected. In the patterned media disk inspection apparatus, plural the optical inspection units and plural the table units are included, and an operation for reversing a substrate by the substrate reversing unit and an operation for taking out a substrate that has already been inspected and supplying an uninspected substrate by the substrate handling unit are alternately performed on the plural the table units.

To address the above-described problems, the present invention further provides a patterned media disk inspection method including irradiating light to one surface of an uninspected patterned media disk, on both surfaces of which a pattern of a resist film is formed and which is taken out from a supply cassette and supplied, by using a first optical inspection unit, spectrally dispersing light reflected from the one surface, and detecting the spectrally dispersed light, and thereby inspecting the pattern of a resist film on the one surface, reversing the patterned media disk in which the pattern of a resist film on the one surface has been inspected by using a disk reversing unit, irradiating light to a surface opposite to the one surface of the reversed patterned media disk by using the first optical inspection unit, spectrally dispersing light reflected from the surface opposite to the one surface, and detecting the spectrally dispersed light, and thereby inspecting a pattern of a resist film on the surface opposite to the one surface, storing the patterned media disk, both surfaces of which have been inspected by the first optical inspection unit, to an accommodation cassette, irradiating light to one surface of an uninspected patterned media disk, on both surfaces of which a pattern of a resist film is formed and which is taken out from a supply cassette and supplied, by using a first optical inspection unit, spectrally dispersing light reflected from the one surface, and detecting the spectrally dispersed light, and thereby inspecting the pattern of a resist film on the one surface, reversing the patterned media disk in which the pattern of a resist film on the one surface has been inspected by using a disk reversing unit, irradiating light to a surface opposite to the one surface of the reversed patterned media disk by using the second optical inspection unit, spectrally dispersing light reflected from the surface opposite to the one surface, and detecting the spectrally dispersed light, and thereby inspecting a pattern of a resist film on the surface opposite to the one surface, and storing the patterned media disk, both surfaces of which have been inspected by the second optical inspection unit, to an accommodation cassette. In the above patterned media disk inspection method, when supplying the uninspected patterned media disk, on both surfaces of which a pattern of a resist film is formed, to the first optical inspection unit from the supply cassette or when storing the patterned media disk, both surfaces of which have been inspected by the first optical inspection unit, to the accommodation cassette, the patterned media disk, one surface of which has been inspected by the second optical inspection unit, is reversed by using the disk reversing unit, and when supplying the uninspected patterned media disk, on both surfaces of which a pattern of a resist film is formed, to the second optical inspection unit from the supply cassette or when storing the patterned media disk, both surfaces of which have been inspected by the second optical inspection unit, to the accommodation cassette, the patterned media disk, one surface of which has been inspected by the first optical inspection unit, is reversed by using the disk reversing unit.

To solve the above-described problems, the present invention further provides a patterned media disk inspection method including inspecting one surface of a patterned media disk, on both surfaces of which a pattern of a resist film is formed, reversing the patterned media disk, the one surface of which has been inspected, by using a disk reversing unit, and inspecting the other reversed surface by using a first and a second optical inspection units. In the patterned media disk inspection method, after inspecting one surface of the patterned media disk by the first optical inspection unit, when reversing the patterned media disk by using the disk reversing unit, a patterned media disk, both surfaces of which have already been inspected by the second optical inspection unit, is taken out from the second optical inspection unit and an uninspected patterned media disk is supplied to the second optical inspection unit, and when taking out the patterned media disk, which is reversed by using the disk reversing unit and in which the other surface has been inspected by the first optical inspection unit to result in both surfaces having been inspected, from the first optical inspection unit and supplying an uninspected patterned media disk to the first optical inspection unit, the patterned media disk, which is supplied to the second optical inspection unit and one surface of which has been inspected by the second optical inspection unit, is reversed by the disk reversing unit.

According to the present invention, it is possible to perform inspection of both surfaces of a patterned media disk while a high throughput is maintained.

These and other objects, features and advantages of the invention will be apparent from the following more particular description of preferred embodiments of the invention, as illustrated in the accompanying drawings.

BRIEF DESCRIPTION OF THE DRAWINGS

FIG. 9 is a flowchart showing a process flow of reversing a patterned media disk, one surface of which has already been inspected, according to the embodiment of the present invention.

DESCRIPTION OF THE PREFERRED EMBODIMENTS

Hereinafter, an embodiment of the present invention will be described with reference to the drawings.

First Embodiment

Figure 1A:
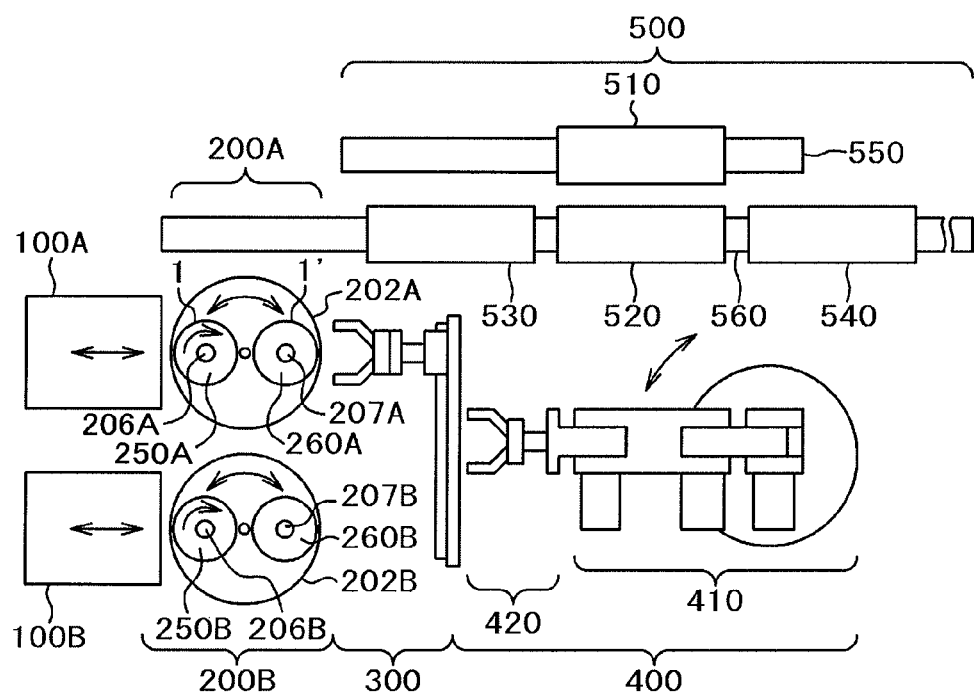
FIG. 1A is a plan view showing a schematic configuration of a patterned media disk inspection apparatus according to an embodiment of the present invention.
Figure 1B:
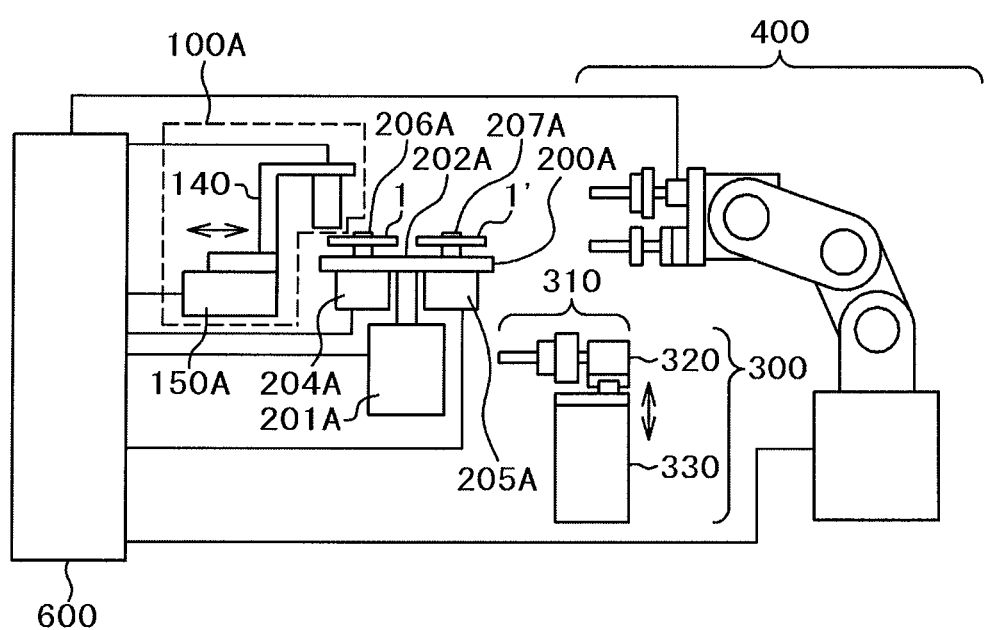
FIG. 1B is a front view showing a schematic configuration of the patterned media disk inspection apparatus according to the embodiment of the present invention.

FIGS. 1A and 1B are diagrams showing an entire configuration of a patterned media disk surface inspection apparatus according to the embodiment. FIG. 1A is a plan view showing a schematic configuration of the patterned media disk surface inspection apparatus according to the embodiment, and FIG. 1B is a front view thereof. In the embodiment, to improve throughput of the inspection apparatus, the inspection apparatus is configured to inspect two patterned media disks at the same time by using two optical inspection devices.

In FIG. 1A, reference numerals 100A and 100E denote optical inspection units, reference numerals 200A and 200B denote table units, reference numeral 300 denotes a substrate reversing unit, reference numeral 400 denotes a substrate handling unit, and reference numeral 500 denotes a cassette unit. In FIG. 1B, reference numeral 600 denotes a signal processing/control unit.

FIG. 1B shows a combination of the optical inspection unit 100A and the table unit 200A.

Figure 2:
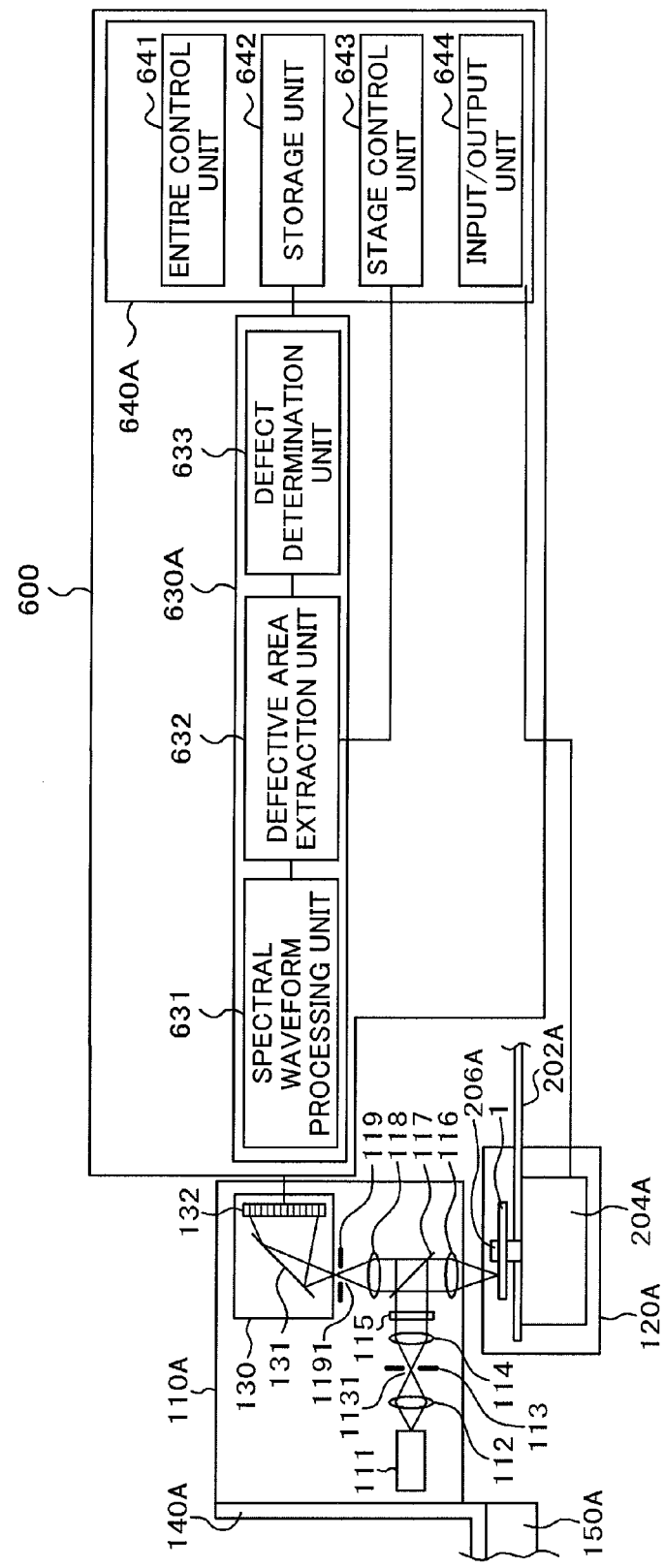
FIG. 2 is a front view showing a schematic configuration of an optical inspection unit according to the embodiment of the present invention.

As shown in FIG. 2, the optical inspection unit 100A is configured to include a detection optical system 110A, a sample rotation drive unit 120A, a linear moving stage 150A, a data processing unit 630A, and a controller 640A. The data processing unit 630A and the controller 640A are mounted in the signal processing/control unit 600 shown in FIG. 1B. The optical inspection unit 100B has the same configuration as that of the optical inspection unit 100A, so the optical inspection unit 100A will be described as an example so as to avoid redundant description.

The detection optical system 110A includes a light source 111 that emits illumination light, a collecting lens 112 that collects the illumination light emitted from the light source 111, a first field diaphragm 113 having a pin hole 1131 that lets the light collected by the collecting lens 112 pass through, a collimating lens 114 that converts the illumination light passing through the pin hole of the first field diaphragm 113 into a parallel light flux, a polarizing plate 115 that adjusts a polarization state of the illumination light passing through the collimating lens 114, a half mirror 117 that switches an optical path of the illumination light whose polarization state is adjusted by the polarizing plate 115 to an optical path to a disk which is a sample 1, an objective lens 116 that collects the illumination light of a parallel light flux whose optical path is switched by the half mirror 117 and irradiates the illumination light to a surface of the sample 1, an imaging lens 118 that collects light, which is reflected from the sample 1 irradiated by the illumination light, and which enters the objective lens 116 again and passes through the half mirror 117, to form an image, a second field diaphragm 119 having a pin hole 1191 that lets the reflected light passing through the imaging lens 118 pass through, a spectroscope 130 that receives the reflected light passing through the second field diaphragm 119.

The spectroscope 130 includes a diffraction grating 131 that receives the reflected light passing through the second field diaphragm 119 and spectrally disperses the reflected light according to wavelengths and a linear detector 132 that divides and detects the light spectrally dispersed by the diffraction grating 131 for each wavelength.

The sample rotation drive unit 120A includes a spindle 206A on which the sample 1 is placed and which rotates the sample 1 and a motor 204A that drives the spindle 206A to rotate.

The linear moving stage 150A has a function to move the detection optical system 110A supported by a support member 140A in a radial direction of the sample 1 according to the rotation of the sample 1 placed on the spindle 206A.

The data processing unit 630A includes a spectral waveform processing unit 631 that A/D-converts a spectral detection signal outputted from the linear detector 132 and obtains a digitalized spectral waveform, a defective area extraction unit 632 that extracts a defective area of the sample 1 placed on the spindle 206A by using spectral reflectance waveform data obtained from spectral waveform data digitalized by the spectral waveform processing unit 631 and stage position information (rotation direction and radial direction) obtained from a stage control unit 643, and a defect determination unit 633 that processes defective area information extracted by the defective area extraction unit 632 and detects a shape defect of a patterned media disk. The defect determination unit 633 further extracts information such as the types of defects, the sizes of defects, and the density of defects by using signals of the detected defects and position information, determines whether or not the defects are within an allowable range, and decides the grade of the inspected substrate (whether the substrate is defective or not).

The controller 640A includes an entire control unit 641, a storage unit 642 that stores inspection data, substrate information, and spectral data, a stage control unit 643 that controls the spindle 206A and the linear moving stage 150A, and an input/output unit 644 that inputs inspection conditions and outputs inspection results.

Next, an operation for inspecting a surface of a patterned media disk by using the optical inspection unit having the configuration shown in FIG. 2 will be described.

Figure 3:
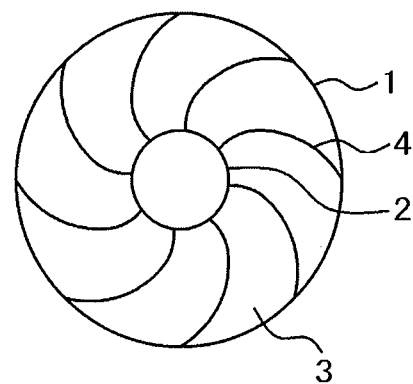
FIG. 3 is a plan view of a patterned media disk.

The sample 1 to be inspected has a planar structure as shown in FIG. 3. The sample 1 has a hole 2 at its center. Data areas 3 storing data on their surfaces and servo areas 4 in which information for controlling a magnetic head (not shown in FIG. 3) that reads/writes data is recorded are alternately formed.

The hole 2 of the sample 1 is fitted with the spindle 206A, so that the sample 1 is supported by the spindle 206A.

While the sample 1 is supported by the spindle 206A, the motor 204A is controlled by the stage control unit 643 and the spindle 206A is rotated at a predetermined speed. At this time, the linear moving stage 150A is controlled by the stage control unit 643 and the linear moving stage 150A is moved in one direction in accordance with the rotation of the spindle 206A. The stage control unit 643 controls rotation position information of the spindle 206A and position information in a linear moving direction of the linear moving stage 150A. The light source 111 emits wideband illumination light (for example, wavelengths are from 200 to 800 nm) including deep ultra violet (DUV) rays. For example, the light source 111 is made of a Xe lamp, halogen lamp, deuterium lamp, or a combination of these.

The illumination light emitted from the light source 111 is collected into the pin hole 1131 provided in the first field diaphragm 113 by the collecting lens 112. An image of the pin hole 1131 formed by the collected illumination light is formed on the surface of the sample 1 via the collimating lens 114 and the objective lens 116 and a detection field is formed. At this time, the polarization state of the illumination light is set by adjusting the polarizing plate 115 so that the illumination light is suitable for the type of the sample 1 (the pattern shape formed on the surface of the sample 1). The half mirror 117 reflects half of the illumination light passing through the polarizing plate 115 to the objective lens 116 and passes the remaining half. As a result, the amount of illumination light irradiated to the sample 1 is half of the amount of illumination light emitted from the light source 111.

The reflected light (specular reflection light) from the sample 1 irradiated by the illumination light is collected by the objective lens 116, half of the amount of the collected light passes through the half mirror 117 and enters the imaging lens 118, and forms an image in the pin hole 1191 of the second field diaphragm 119.

The pin hole 1191 provided in the second field diaphragm 119 is formed corresponding to the size of the image of the pin hole 1131 of the first field diaphragm 113, which is projected onto the sample 1, and the second field diaphragm 119 blocks stray light and light that does not form an image in the pin hole 1191.

The reflected light from the sample 1, which passes through the pin hole 1191 provided in the second field diaphragm 119, reaches the diffraction grating 131 of the spectroscope 130. The reflected light from the sample 1, which reaches the diffraction grating 131, is spectrally dispersed and reflected according to wavelengths, and detected by the linear detector 132.

The spectral waveform detected by the linear detector 132 is inputted into the spectral waveform processing unit 631, A/D-converted, and digitalized. The digitalized spectral waveform is transmitted to the defective area extraction unit 632. The defective area extraction unit 632 receives position information of the rotation direction of the spindle 206A and the radial direction of the sample 1 of the linear moving stage 150A from the stage control unit 643, processes the digitalized spectral waveform, and extracts a defective area on the sample 1.

Next, in the configuration shown in FIGS. 1A and 1B, the table units 200A and 200B respectively include tables 202A and 202B that can be respectively driven and rotated by motors 201A and 201B.

The table 202A is driven by the motor 201A and bi-directionally rotates 180 degrees, so the table 202A moves positions of the spindles 206A and 207A between an inspection position 250A (position of the patterned media disk 1 in FIG. 1A) and a substrate transferring/reversing position 260A (position of the patterned media disk 1' in FIG. 1A).

Similarly, the table 202B is driven by the motor 201B and bi-directionally rotates 180 degrees.

The substrate handling unit 400 includes an articulated robot 410 and a chuck unit 420 attached to the tip of the articulated robot 410. In the chuck unit 420, an upper and lower pair of chucks are mounted on a base plate 427 supported by the articulated robot 410.

Figure 4:
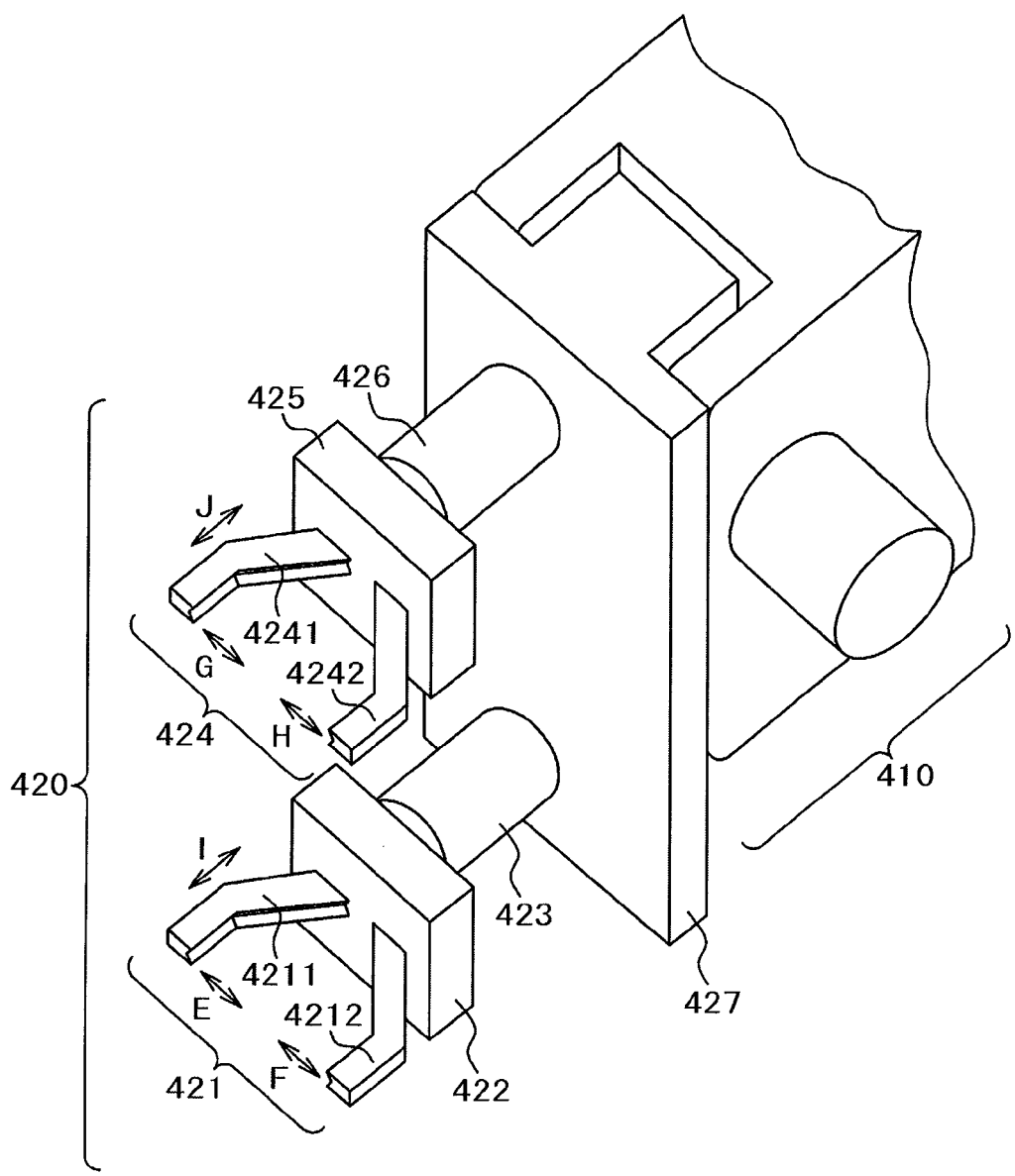
FIG. 4 is a perspective view showing a configuration of a chuck unit of a substrate handling unit according to the embodiment of the present invention.

FIG. 4 shows a configuration of the chuck unit 420. A chuck 421 for providing a new patterned media disk to the table units 200A and 200B is mounted on a lower portion, and a chuck 424 for taking out a patterned media disk that has already been inspected from the table units 200A and 200B is mounted on an upper portion.

The chuck 421 on the lower portion has a pair of hooks 4211 and 4212. The pair of hooks 4211 and 4212 are driven by a hook drive unit 422, so the pair of hooks 4211 and 4212 open and close in the directions indicated by the arrows E and F in FIG. 4, and hold or release the patterned media disk 1. Further, the hook drive unit 422 is moved in a front-back direction (direction indicated by the arrow I) by an arm cylinder 423 fixed to the base plate 427.

Similarly, the chuck 424 on the upper portion has a pair of hooks 4241 and 4242. The pair of hooks 4241 and 4242 are driven by a hook drive unit 425, so the pair of hooks 4241 and 4242 open and close in the directions indicated by the arrows G and H in FIG. 4, and hold or release the patterned media disk 1. Further, the chuck 424 is moved in a front-back direction (direction indicated by the arrow J) by an arm cylinder 426 fixed to the base plate 427.

Figure 5:
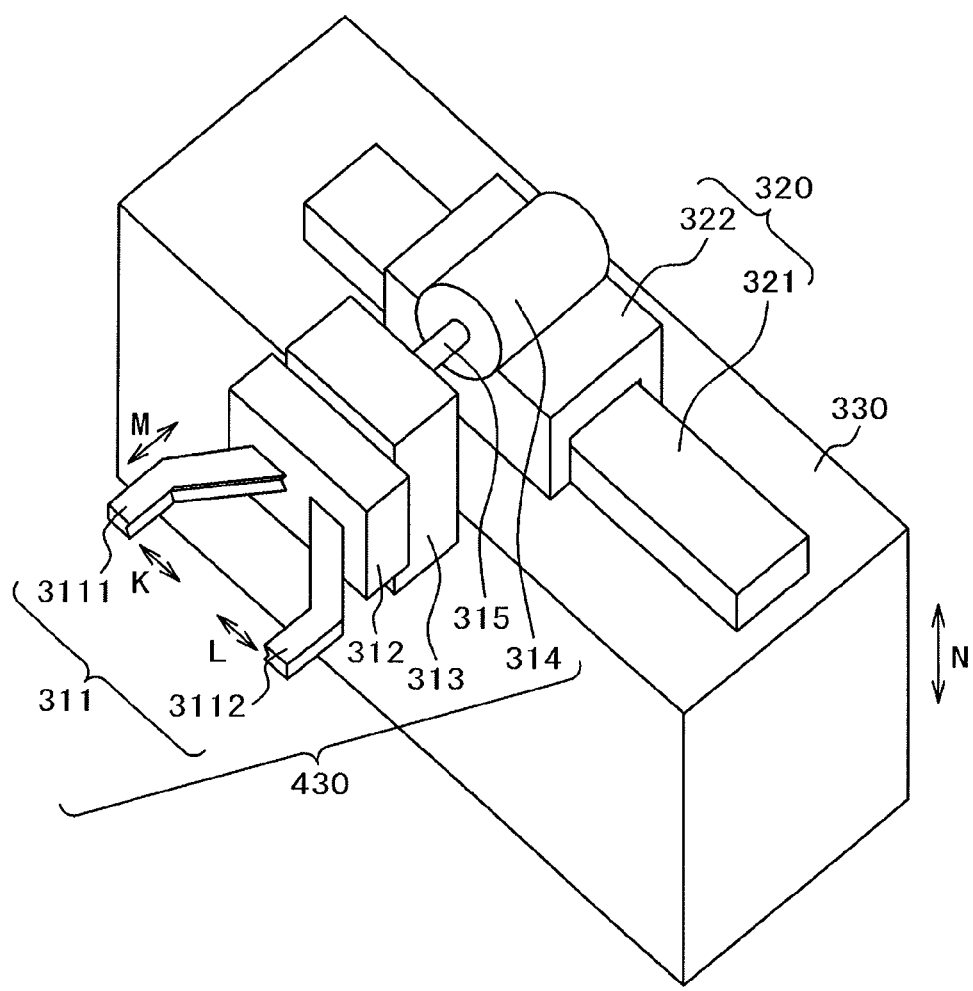
FIG. 5 is a perspective view showing a configuration of a chuck unit of a substrate reversing unit according to the embodiment of the present invention.

FIG. 5 shows a configuration of the substrate reversing unit 300. The substrate reversing unit 300 includes a substrate chuck unit 310, a slide guide unit 320, and a vertical drive unit 330. The substrate chuck unit 310 has a chuck 311 including a pair of hooks 3111 and 3112 and a hook drive unit 312 for driving the pair of hooks 3111 and 3112 to open and close. The hook drive unit 312 drives the pair of hooks 3111 and 3112 to open and close in order to hold or release the patterned media disk 1. The hook drive unit 312 and the pair of hooks 3111 and 3112 are rotated 180 degrees by a hook reverse drive unit 313, so that the patterned media disk 1 that is sandwiched and held by the pair of hooks 3111 and 3112 is reversed to be upside down. The hook reverse drive unit 313, the hook drive unit 312, and the pair of hooks 3111 and 3112 are moved in a front-back direction (direction indicated by the arrow M) by a guide shaft 315 extended from a front-back drive cylinder 314.

The front-back drive cylinder 314 is fixed to an X table 322 which includes a drive source (not shown in FIG. 5) inside thereof and moves along a guide rail 321 fixed to a vertical drive unit 330. The vertical drive unit 330 is driven in a vertical direction (direction indicated by the arrow N) by a drive source not shown in FIG. 5.

The cassette unit 500 shown in FIG. 1A includes a supply cassette 510, a non-defective disk cassette 520 that accommodates patterned media disks which are determined to be non-defective, a single side defective disk cassette 530 that accommodates patterned media disks, one side of which is determined to be defective, and a double side defective disk cassette 540 that accommodates patterned media disks, both sides of which are determined to be defective. (The supply cassette 510, the single side defective disk cassette 530, and the double side defective disk cassette 540 are collectively referred to as "accommodation cassette"). These cassettes can be moved along a rail 550 or a rail 560.

Figure 6:
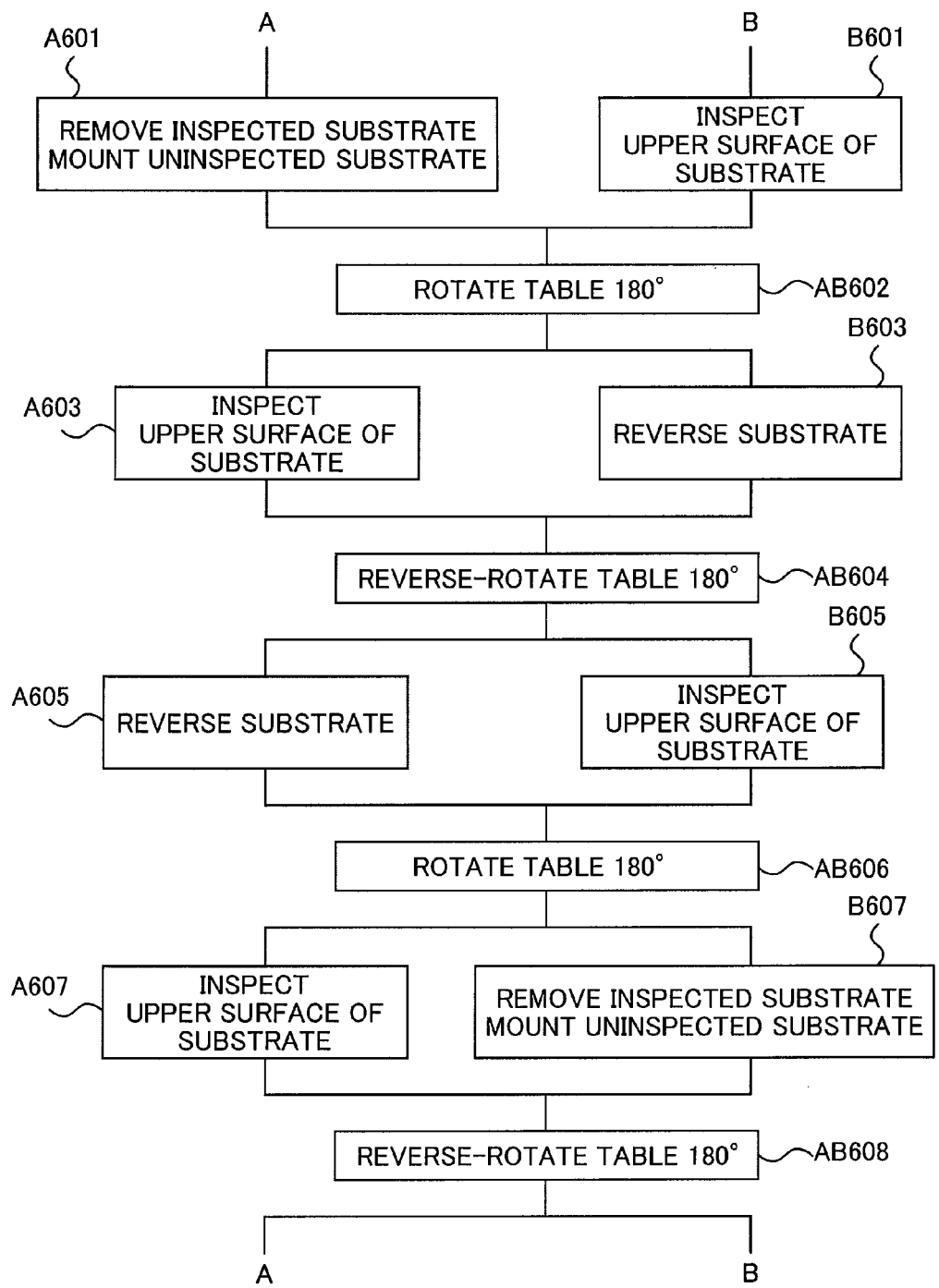
FIG. 6 is a flowchart showing a process flow of the patterned media disk inspection apparatus according to the embodiment of the present invention.

With reference to FIG. 6, a series of operations will be described, in which both sides of a patterned media disk taken out from the supply cassette 510 are inspected by the optical inspection unit 100A and the optical inspection unit 100B and the patterned media disk is accommodated in one of the non-defective disk cassette 520, the single side defective disk cassette 530, and the double side defective disk cassette 540.

A process performed by a combination of the optical inspection unit 100A and the table 202A (inspection unit A) will be described with reference to FIG. 6.

In FIG. 6, alphabet A shows a process performed on a substrate (patterned media disk) held by the spindle 207A, and alphabet B shows a process performed on a substrate (patterned media disk) held by the spindle 206A.

First, at the substrate transferring/reversing position 260A, a substrate, both sides of which have already been inspected, is removed from the spindle 207A by the substrate handling unit 400, and a new substrate is mounted on the spindle 207A by the substrate handling unit 400 (A601). On the other hand, at the inspection position 250A, one side (upper surface) of a substrate held by the spindle 206A is inspected by using the optical inspection unit 100A (B601). Next, the table 202A is rotated 180 degrees, the substrate which is newly mounted on the spindle 207A at the substrate transferring/reversing position 260A is moved to the inspection position 250A, and the substrate which has already been inspected at the inspection position 250A and which is held by the spindle 206A is moved to the substrate transferring/reversing position 260A (AB602).

Next, one side of the substrate held by the spindle 207A is inspected by using the optical inspection unit 100A at the inspection position 250A (A603). The substrate held by the spindle 206A is removed from the spindle 206A and reversed by the substrate reversing unit 300 at the substrate transferring/reversing position 260A, and the substrate is mounted on the spindle 206A again by the substrate reversing unit 300 with the side that has not yet been inspected facing up (B603). Next, when the substrate reversing unit 300 moves back to a retracted position, the table 202A is reversely rotated 180 degrees, so that the spindle 207A holding the substrate, one side of which has already been inspected at the inspection position 250A, is moved to the substrate transferring/reversing position 260A and the spindle 206A holding the reversed substrate is moved to the inspection position 250A (AB604).

Next, the substrate reversing unit 300 moves to the substrate transferring/reversing position 260A, the substrate reversing unit 300 takes out the substrate held by the spindle 207A, one side of which has already been inspected, and reverses the substrate, and the substrate reversing unit 300 mounts the substrate on the spindle 207A again with the side that has not yet been inspected facing up (A605). On the other hand, at the inspection position 250A, the other side of the substrate held by the spindle 206A, one side of which has already been inspected, is inspected (B605). Next, the table 202A is rotated 180 degrees, the spindle 207A holding the substrate that is reversed by the substrate reversing unit 300 is moved to the inspection position 250A, and the spindle 206A holding the substrate, both sides of which have already been inspected, is moved to the substrate transferring/reversing position 260A (AB606).

Next, at the inspection position 250A, the substrate that is reversed and held by the spindle 207A is inspected by using the optical inspection unit 100A (A607). On the other hand, at the substrate transferring/reversing position 260A, the substrate held by the spindle 206A, both sides of which have already been inspected, is removed from the spindle 206A by the substrate handling unit 400, and a new substrate is mounted on the spindle 206A by the substrate handling unit 400 (B607). Next, the table 202A is reversely rotated 180 degrees, so that the spindle 207A holding the substrate, both sides of which have already been inspected at the inspection position 250A, is moved to the substrate transferring/reversing position 260A, and the spindle 206A holding the newly supplied substrate is moved to the inspection position 250A (AB608). Thereafter, the operations from A601 and B601 to AB608 are repeatedly performed.

A process performed by a combination of the optical inspection unit 100B and the table 202B (inspection unit B) is the same as that performed by the combination of the optical inspection unit 100A and the table 202A (inspection unit A) described above, but the timing of the process is different. Specifically, the inspection unit B performs the process of A605 and B605 at the timing when the inspection unit A performs the process of A601 and B601. Thereafter, the process is performed in the sequence described in the flowchart shown in FIG. 6. Specifically, when the inspection unit A performs the substrate reversing process (B603, A605), the inspection unit B performs the inspected substrate removing/uninspected substrate mounting process (A601, B607). In this way, the timings of the processes of the inspection unit A and the inspection unit B are shifted from each other, so that the substrate handling unit 400 and the substrate reversing unit 300 can be shared. Thereby, it is not necessary to prepare plural substrate handling units 400 and substrate reversing units 300, so that space can be saved.

Figure 7:
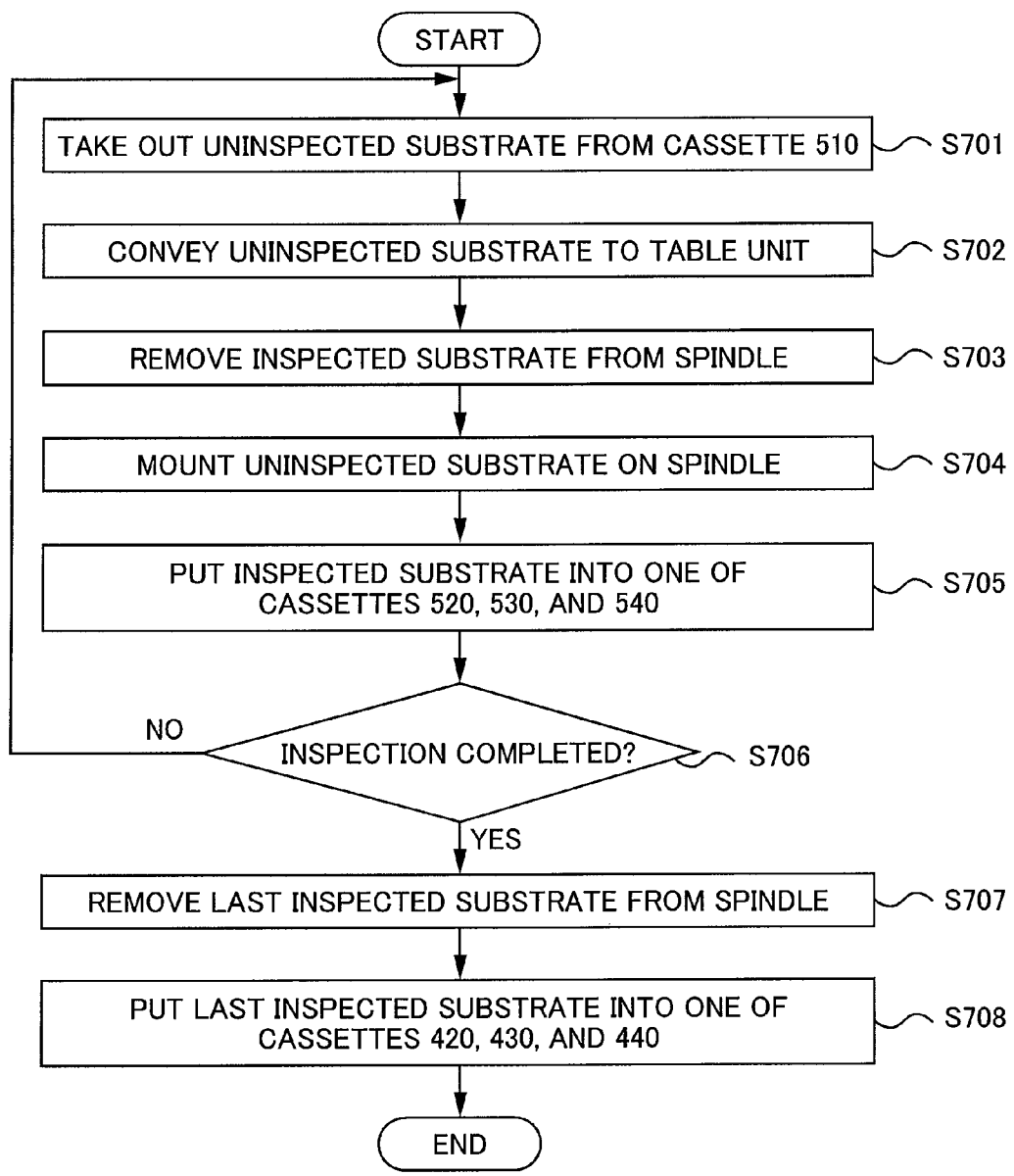
FIG. 7 is a flowchart showing a detailed process flow of "remove inspected substrate" and "mount uninspected substrate" in steps A601 and B607 in the process flow of the patterned media disk inspection apparatus according to the embodiment of the present invention.

FIG. 7 shows a detailed flowchart of the operation of the substrate handling unit 400 regarding the process, which is performed in A601 and B607 in the process flow described in FIG. 6, and in which the substrate, both sides of which have already been inspected, is removed from the spindle 206A or 207A by using the substrate handling unit 400 and a new uninspected substrate which is conveyed from the supply cassette 510 is mounted on the spindle 206A or 207A. The operation in which a substrate is mounted on or removed from the spindles 206B and 207B of the table unit 200B is substantially the same as the above operation, so that the description thereof will be omitted.

First, the chuck unit 420 is moved to a position of the supply cassette 510 by driving the articulated robot 410 of the substrate handling unit 400, and one of substrates standing upright vertically in a row in the supply cassette 510 is taken out from the supply cassette 510 by chucking the substrate by the chuck 421 (S701). Next, the articulated robot 410 swivels and conveys the substrate taken out from the supply cassette 510 to the substrate transferring/reversing position 260A of the table unit 200A (S702). Next, a substrate, both sides of which have already been inspected, is chucked by the chuck 424 and removed from the spindle 207A (S703), and the new substrate which is chucked by the chuck 421 and conveyed from the supply cassette 510 is mounted on the spindle 207A (S704). Next, the substrate removed from the spindle 207A, both sides of which have already been inspected, is accommodated in one of the non-defective disk cassette 520, the single side defective disk cassette 530, and the double side defective disk cassette 540 according to the result of the inspection (S705).

Next, whether or not all the substrates have been conveyed from the supply cassette 510 to the substrate inspection device is checked (S706), and if a substrate to be inspected remains in the supply cassette 510, the process returns to S701 and the process is continuously performed. On the other hand, if all the substrates have been conveyed, when the substrate conveyed last has been inspected, the substrate is removed from the spindle 207A (S707), and the removed substrate is accommodated in one of the non-defective disk cassette 520, the single side defective disk cassette 530, and the double side defective disk cassette 540 according to the result of the inspection (S708), and then the inspection is completed.

Figure 8:
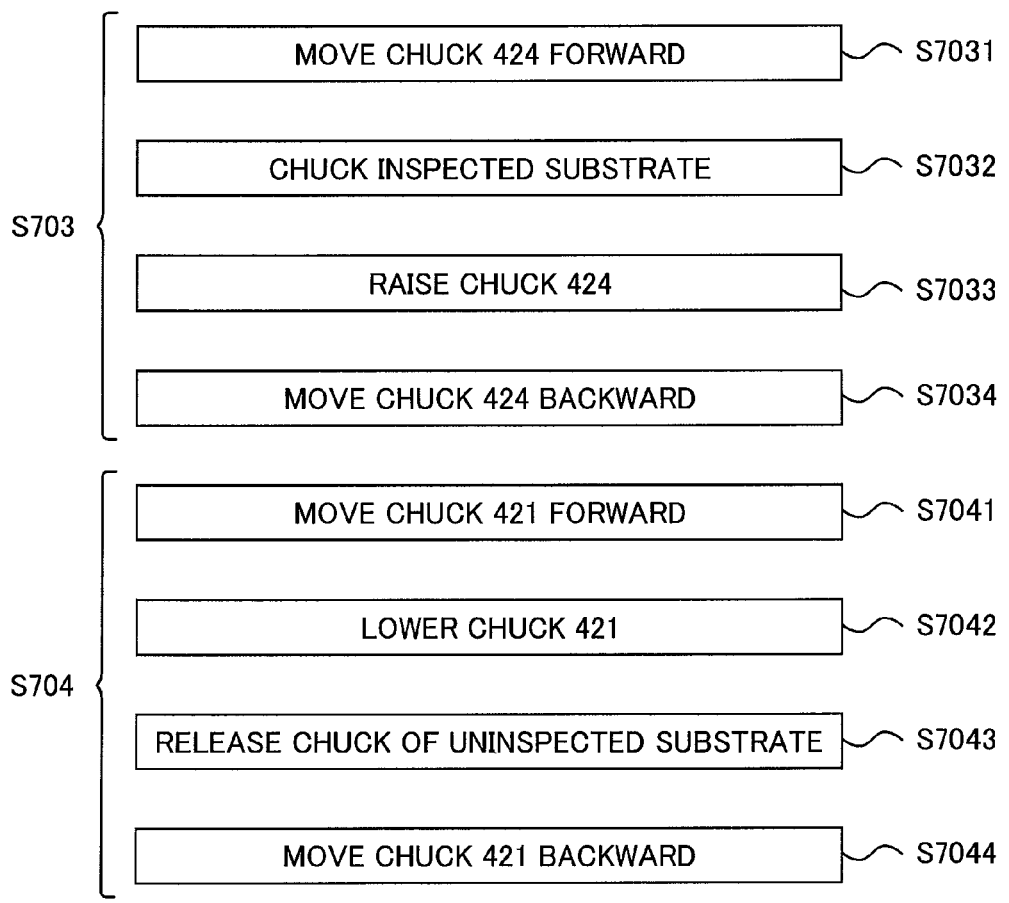
FIG. 8 is a flowchart showing a detailed process flow of steps S703 and S704 in the process flow shown in FIG. 7 according to the embodiment of the present invention.

FIG. 8 shows a detailed flowchart of the operation of the chuck unit 420 in the process of S703 in which the substrate, both sides of which have already been inspected, is removed from the spindle 207A and the process of S704 in which an uninspected substrate which is conveyed from the supply cassette 510 is mounted on the spindle 207A, which are described in FIG. 7.

First, in step S703, by controlling the articulated robot 410 by the entire control unit 641, while the chuck 424 of the chuck unit 420 faces the substrate transferring/reversing position 260A of the table 202A, the hooks 4241 and 4242 are opened by the hook drive unit 425 and the chuck 424 is moved forward by actuating the arm cylinder 426 (S7031). When the chuck 424 is moved forward to a predetermined position, the hooks 4241 and 4242 are operated to be closed by the hook drive unit 425, so that the substrate, both sides of which have already been inspected, and which is held by the spindle 207A at the substrate transferring/reversing position 260A, is sandwiched and held by the hooks 4241 and 4242 (S7032).

Next, by controlling the articulated robot 410 while the substrate is sandwiched and held by the chuck 424, the chuck unit 420 is raised until the position of the new substrate held by the chuck 421 becomes higher than the upper end of the spindle 207A (S7033), and the substrate sandwiched and held by the chuck 424 is removed from the spindle 207A. Next, the chuck 424 that chucks the substrate removed from the spindle 207A, both sides of which have already been inspected, is moved backward by actuating the arm cylinder 426 (S7034).

Next, in step S704, by actuating the arm cylinder 423, the chuck 421 is moved forward until the new substrate held by the chuck 421 comes to a position immediately above the spindle 207A (S7041). Next, by controlling the articulated robot 410, the chuck unit 420 is lowered (S7042) and the new substrate held by the chuck 421 is mounted on the spindle 207A, and then the hooks 4211 and 4212 are operated to be opened by the hook drive unit 422 and the chuck is released by the hook drive unit 422 (S7043). Next, by actuating the arm cylinder 423 while the hooks 4211 and 4212 are opened, the chuck 421 is moved backward (S7044), so that the loading of the new substrate to the spindle 207A is completed.

Next, the substrate reversing process performed in steps B603 and A605 in FIG. 6 will be described with reference to FIG. 9. First, in an initial state, to avoid interference with the substrate handling unit 400, the substrate reversing unit 300 stands by in a state in which the substrate chuck unit 310 is lowered most (at the lower end) by actuating the vertical drive unit 330. In this state, in step B603, the substrate is reversed at the substrate transferring/reversing position 260A of the table unit 200A. In this substrate reversing operation, first, the X table 322 is moved along the guide rail 321 until the substrate chuck unit 310 reaches the substrate transferring/reversing position 260A of the table unit 200A (S901). Next, by actuating the vertical drive unit 330, the substrate reversing unit 300 is raised to a position at which the pair of hooks 3111 and 3112 of the substrate chuck unit 310 face the substrate, the upper surface of which has already been inspected, and which is held by the spindle 207A at the substrate transferring/reversing position 260A (S902).

Next, the substrate chuck unit 310 is moved forward to a predetermined position by actuating the arm cylinder 314 while the hooks 3111 and 3112 of the chuck 311 are opened by the hook drive unit 312 (S903). When the substrate chuck unit 310 reaches the predetermined position, the hooks 3111 and 3112 of the chuck 311 are operated to be closed by the hook drive unit 312, and the substrate, the upper surface of which has already been inspected, and which is held by the spindle 207A (or 206A) at the substrate transferring/reversing position 260A, is sandwiched and held by the hooks 3111 and 3112 of the chuck 311 (S904). Next, the substrate chuck unit 310 is raised by actuating the vertical drive unit 330 while the substrate is sandwiched and held by the chuck 311 (S905), and the chuck 311 is rotated 180 degrees by the hook reverse drive unit 313, so that the substrate sandwiched and held by the chuck 311 is reversed and the surface which has not yet been inspected faces up (S906).

Next, the substrate chuck unit 310 is lowered by actuating the vertical drive unit 330 (S907), and the substrate sandwiched and held by the chuck 311 is mounted on the spindle 207A (or the spindle 206A). Next, the substrate is released by actuating the hooks 3111 and 3112 to open by the hook drive unit 312 (S908), and the substrate chuck unit 310 is moved backward to a predetermined position by actuating the arm cylinder 314 (S909). After the arm cylinder 314 moves the substrate chuck unit 310 backward to the predetermined position, the substrate chuck unit 310 is lowered to a retracted position by actuating the vertical drive unit 330 (S910), and a series of operations is completed.

When the substrate is reversed on the side of the table unit 200B at the timing of A601 and B607 in FIG. 6, in a step corresponding to S901, the X table 322 is moved along the guide rail 321 until the substrate chuck unit 310 reaches the substrate transferring/reversing position 260B of the table unit 200B, and thereafter processes corresponding to S902 to S910 are performed.

Although, in the embodiment, an example of a configuration is described in which the substrate reversing unit 300 includes the substrate chuck unit 310, the slide guide unit 320, and the vertical drive unit 330, the slide guide unit 320 and the vertical drive unit 330 may be replaced by a robot similar to the articulated robot 410 of the substrate handling unit 400, or may be replaced by a scalar type robot.

As described above, according to the embodiment, in the patterned media surface inspection apparatus including two inspection units in which an optical inspection unit and a table unit are combined, the substrate handling unit 400 and the substrate reversing unit 300 are shared, so that it is possible to suppress an increase in an installation area (footprint) of the entire apparatus while a high throughput is maintained.

Further, according to the present invention, it is possible to perform inspection of both surfaces of a patterned media disk while a high throughput is maintained.

The invention may be embodied in other specific forms without departing from the spirit or essential characteristics thereof. The present embodiment is therefore to be considered in all respects as illustrative and not restrictive, the scope of the invention being indicated by the appended claims, rather than by the foregoing description, and all changes which come within the meaning and range of equivalency of the claims are therefore intended to be embraced therein.

The invention claimed is:

1. A patterned media disk inspection apparatus, comprising:
    an optical inspection unit that emits light to one surface of a substrate, on both surfaces of which a pattern of a resist film is formed, detects a spectrum of light reflected from the pattern, and inspects the pattern;
    a table unit including a plurality of substrate rotation drive units on which the substrate is mounted and rotated, the table unit rotating and conveying substrates mounted on the substrate rotation drive units between a position at which the substrate is inspected by the optical inspection unit and a position at which the substrate is taken out and supplied;
    a substrate reversing unit that removes the substrate, which is mounted on the substrate rotation drive unit and one surface of which is inspected by the optical inspection unit and further which is rotated and conveyed to the position at which the substrate is taken out and supplied by the table unit, from the substrate rotation drive unit, reverses the substrate, and thereafter mounts again the substrate on the substrate rotation drive unit;
    a cassette unit including a cassette that accommodates a substrate that has not yet been inspected and a cassette that accommodates a substrate that has already been inspected; and
    a substrate handling unit having a chuck for supplying an uninspected substrate and a chuck for taking out an inspected substrate, where the substrate handling unit takes out an uninspected substrate with the chuck for supplying from the cassette that accommodates a substrate that has not yet been inspected and supplies the uninspected substrate to one of the substrate rotation drive units of the table unit, and further takes out the substrate with the chuck for taking out, where both surfaces of the substrate have been inspected by the optical inspection unit, from the one of the substrate rotation drive units and stores the substrate in the cassette that accommodates a substrate that has already been inspected after the uninspected substrate chucked by the chuck for supplying is supplied to the substrate rotation drive units,
    wherein a plurality of the optical inspection units and a plurality of the table units are included, and an operation for reversing a substrate by the substrate reversing unit and an operation for taking out a substrate that has already been inspected and supplying an uninspected substrate by the substrate handling unit are alternately performed on the plurality of the table units.

2. The patterned media disk inspection apparatus according to claim 1, further comprising: a moving unit that moves between the plurality of table units.

3. The patterned media disk inspection apparatus according to claim 1, wherein the substrate handling unit includes an articulated robot and both of the chucks for supplying and for taking out are attached to a tip of the articulated robot.

* * * * *